(12) United States Patent
Daggett

(10) Patent No.: US 12,115,301 B2
(45) Date of Patent: *Oct. 15, 2024

(54) PERCUTANEOUS ENDOSCOPIC GASTRONOMY TUBE FOR OPTIMIZED GASTRIC SUMPING

(71) Applicant: University Of South Florida, Tampa, FL (US)

(72) Inventor: Justin Robert Daggett, Denver, NC (US)

(73) Assignee: University of South Florida, Tampa, FL (US)

( * ) Notice: Subject to any disclaimer, the term of this patent is extended or adjusted under 35 U.S.C. 154(b) by 1477 days.

This patent is subject to a terminal disclaimer.

(21) Appl. No.: 16/527,113

(22) Filed: Jul. 31, 2019

(65) Prior Publication Data

US 2019/0351110 A1 Nov. 21, 2019

Related U.S. Application Data

(63) Continuation of application No. 15/829,329, filed on Dec. 1, 2017, now Pat. No. 10,376,619, which is a continuation of application No. 14/720,307, filed on May 22, 2015, now Pat. No. 9,867,915.

(60) Provisional application No. 62/023,268, filed on Jul. 11, 2014.

(51) Int. Cl.
*A61M 1/00* (2006.01)

(52) U.S. Cl.
CPC ..... *A61M 1/964* (2021.05); *A61M 2210/1053* (2013.01)

(58) Field of Classification Search
CPC ........ A61M 1/0088; A61M 2039/0261; A61M 25/04; A61M 2210/1053; A61J 5/0015; A61J 5/003

See application file for complete search history.

(56) References Cited

U.S. PATENT DOCUMENTS

| | | | |
|---|---|---|---|
| 2,470,665 A | 5/1949 | Stiehl | |
| 2,492,384 A | 12/1949 | Kaslow | |
| 3,114,373 A | 12/1963 | Andersen | |
| 3,421,510 A | 1/1969 | Kettenbach | |
| 3,915,171 A * | 10/1975 | Shermeta | A61J 15/0065 D24/112 |
| 3,999,554 A | 12/1976 | Kim et al. | |
| 4,356,824 A | 11/1982 | Vazquez | |
| 4,666,433 A | 5/1987 | Parks | |
| 5,273,523 A | 12/1993 | Sozuki et al. | |

(Continued)

*Primary Examiner* — Lauren P Farrar
(74) *Attorney, Agent, or Firm* — Nicholas Pfeifer Smith & Hopen, P. A.

(57) ABSTRACT

An improved percutaneous endoscopic gastrostomy (PEG) tube that allows continuous suctioning/sumping without occlusion of the tube by the gastric wall. The PEG tube includes a hollow drainage tubing coupled to a ventilated bell cap. The bell cap can be open or closed to the external environment is ventilated via apertures, crenellations and grooves, and hemispherical arches. The PEG tube minimizes, or completely eliminates, the need for a user thereof to frequently flush the tube, thus also curtailing intermittent suctioning and allowing for longer periods of uninterrupted drainage. Furthermore, the PEG tubes of the current invention reduce clogging of the tube by larger gastric matter that is intended to be suctioned out of the patient or subject.

11 Claims, 11 Drawing Sheets

(56) References Cited

U.S. PATENT DOCUMENTS

| | | | | |
|---|---|---|---|---|
| 5,356,391 | A | * | 10/1994 | Stewart ............... A61J 15/0015 |
| | | | | 604/174 |
| 5,391,159 | A | | 2/1995 | Hirsch et al. |
| 6,030,361 | A | * | 2/2000 | Miyashiro ............. A61M 25/04 |
| | | | | 604/523 |
| 6,322,538 | B1 | | 11/2001 | Elbert et al. |
| 7,582,072 | B2 | | 9/2009 | McMichael |
| 9,867,951 | B2 | | 1/2018 | Daggett |
| 2007/0060823 | A1 | | 3/2007 | Giroux et al. |
| 2014/0276502 | A1 | * | 9/2014 | Cisko ..................... A61F 5/451 |
| | | | | 604/355 |

* cited by examiner

PERCUTANEOUS ENDOSCOPIC GASTRONOMY TUBE FOR OPTIMIZED GASTRIC SUMPING

CROSS-REFERENCE TO RELATED APPLICATIONS

This nonprovisional application is a continuation of and claims priority to currently pending U.S. Nonprovisional patent application Ser. No. 15/829,329, entitled "Percutaneous Endoscopic Gastronomy Tube for Optimized Gastric Sumping", filed Dec. 1, 2017, which is a continuation of and claims priority to U.S. Nonprovisional patent application Ser. No. 14/720,307, entitled "Percutaneous Endoscopic Gastronomy Tube for Optimized Gastric Sumping", filed May 22, 2015 and issued on Jan. 16, 2018 as U.S. Pat. No. 9,867,915, which is a continuation of and claims priority to Provisional Patent Application No. 62/023,268, entitled "Percutaneous Endoscopic Gastronomy Tube for Optimized Gastric Sumping", filed Jul. 11, 2014 by the same inventor, all of which are incorporated herein in their entireties.

BACKGROUND OF THE INVENTION

1. Field of the Invention

This invention relates, generally, to percutaneous endoscopic gastronomy ("PEG"). More specifically, it relates to an improved PEG tube for optimized gastric sumping.

2. Brief Description of the Prior Art

A standard PEG tube has an intragastric "bell" that resembles the underside of a mushroom cap which holds it in place and prevents it from being pulled free of the abdominal wall (see FIGS. 1A and 1B). When a PEG tube is placed to suction for purposes of gastric drainage this bell frequently contacts the opposite stomach wall creating a seal and preventing further drainage (see FIG. 1B), thus hindering the therapy.

As noted, PEG and nasogastric tubes are known in the art. For example, U.S. Pat. No. 5,356,391 to Stewart discloses a collapsible gastrostomy tube having a collapsible, internal retention flange. The gastrostomy tube is inserted into a patient's stomach by a percutaneous endoscopic or other suitable technique. However, the internal retention flange comprises a dome shape that would adhere to the contralateral stomach wall when suction is applied, effectively sealing off the tube.

U.S. Pat. No. 5,391,159 to Hirsch et al. discusses a gastrostomy tube is a flexible tube having on one inner end thereof an improved energy absorbent internal retaining member. The energy absorbent internal retaining member has a hollow body portion with two resiliently reversible physical forms or shapes, toroidal-like, and, goblet-like connected to a foreshortened hollow axial stem portion that is attached to or integrally made with the inward end of the flexible tube. The internal retaining member is made in the toroidal-like form. During intentional removal, when under pressure against the stomach mucosa, the internal retaining member snaps into the unrolled, dome-like shape and pulls out through the stoma tract. However, the dome-shaped retaining member still would adhere to the contralateral stomach wall when suction is applied, effectively sealing off the tube.

U.S. Pat. No. 3,421,510 to Kettenbach discloses a design for a temporarily placed surgical drain. These drains are placed around viscera or in the soft tissue as a temporary treatment after surgery and removed after several days. They cannot, however, be placed into the actual lumens of viscera.

U.S. Pat. No. 5,273,523 to Sozuki et al. discusses a design modification for a nasogastric tube. These tubes are placed through the nose into the stomach and are considered a temporary treatment. While these are well adapted for suctioning/sumping the stomach, they are temporary and cannot be inserted through an abdominal wall.

Similarly, U.S. Patent App. Pub. No. 2007/0060823 to Giroux et al. describes suction venting on a nasogastric tube provided by a sump lumen within the tube and not by a geometric property of the tube itself. These nasogastric tubes are not typically used for long term feeding, as is often done with a PEG tubes due to the long and narrow lumen which is prone to clogging. U.S. Pat. No. 3,999,554 to Kim et al. and U.S. Pat. No. 3,114,373 to Andersen describes a similar nasogastric tube as that seen in U.S. Pat. No. 5,273,523 to Sozuki et al. and U.S. Patent App. Pub. No. 2007/0060823 to Giroux et al. and include the same drawbacks as the described nasogastric publications. Similarly, U.S. Pat. No. 2,492,384 to Kaslow relates to nasogastric tubes as well. While the loop design at the end of this tube could theoretically help prevent occlusion, given the pliability of gastric mucosa, this is unlikely, and again this tube could not be used percutaneously.

U.S. Pat. No. 4,356,824 to Vazquez applies the principles of a nasogastric tube but placed through a gastric tube base. The suction tube utilizes a second interior sump tube to prevent sealing. This design facilitates the prevention of sealing or clogging, but does so by effectively adding several additional tubes and lumens, rather than any geometric alteration of the PEG tube bell itself. Additionally, this tube could not be placed percutaneously via an endoscope as it has multiple tubes and lumens on each end and could not be pulled through a single skin hole and would require a full surgical laparotomy.

U.S. Pat. No. 2,470,665 to Stiehl discloses a suction tip for a tube utilizing an inflatable hood to keep the stomach walls away from the suction tubing to prevent occlusion of the suction ports. However, this apparatus requires inclusion of additional ports on the proximal end of the tube, meaning that it cannot be placed percutaneously like a PEG tube.

Accordingly, what is needed is an improved PEG tube that can more effectively sump or suction out the contents of a body lumen, such as the stomach. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for a ventilated PEG tube is now met by a new, useful, and nonobvious invention.

In an embodiment, the current invention is a percutaneous endoscopic gastrostomy tube apparatus. The apparatus includes an elongate, substantially hollow drainage tubing that has proximal and distal ends. The drainage tubing is configured to extend through a patient or subject's body with the distal end of the drainage tubing being positioned in a region of interest (e.g., stomach lumen) within the patient or subject's body. A bell cap is coupled to the distal end of the drainage tubing and has a substantially hollow interior in open communication with the interior the drainage tubing. The bell cap has a distal end and also a distal edge at the distal-most portion of the distal end of the bell cap. The apparatus further includes a means of ventilating the bell cap, where the ventilating means is positioned through and along a body of the bell cap and/or through and along the distal edge of the bell cap. This allows the interior of the bell cap to be in open communication with an external environment through the ventilating means.

Optionally, the drainage tubing can include a plurality of channels extending therethrough along a length of the drainage tubing, where one of the channels is a drainage lumen and the other channel is a ventricular lumen.

The distal end of the bell cap may be open or closed to the external environment. When open, the ventilating means may be a plurality of apertures disposed about the circumference of the body of the bell cap. In this case, each aperture can have a diameter that is equal to or less than a diameter of the distal end of the drainage tubing. Alternatively, when the distal end of the bell cap is open to the external environment, the ventilating means can be a plurality of crenellations disposed along the distal edge of the bell cap, such that a groove is formed between each pair of crenellations around the distal edge of the bell cap. In this case, the groove may have a width or length that is equal to or less than a diameter of the distal end of the drainage tubing.

Alternatively, when the distal end of the bell cap is open to the external environment, the ventilating means can be a hemispherical arch attached to the bell cap at two (2) distinct points on the bell cap and extending distally from the bell cap to a distal apex positioned at a spaced distance away from (distal to) the distal edge of the bell cap. These two (2) distinct points of connection between the hemispherical arch and the bell cap may be in diametric opposition to each other. Optionally, the ventilating means may include a second hemispherical arch attached to the bell at another two (2) distinct points on the bell cap and extending distally to a distal apex positioned at a spaced distance away from (distal to) the distal edge of the bell cap. In this case, these additional two (2) distinct points of connection between the second hemispherical arch and the bell cap may be in diametric opposition to each other. Further, the two hemispherical arches can intersect each other at the distal apexes, such that the spaced distances away from the bell cap are about the same distance away from the bell cap. In other words, the two hemispherical arches would share one apex. Alternatively, the hemispherical arches can intersect, such that one has a further distal apex than the other. In either case, the intersection between the hemispherical arches can form a ninety (90) degree angle between each other.

When the distal end of the bell cap is closed to the external environment, the ventilating means can be an array of apertures formed through and along a surface of the body of the bell cap. Each aperture can have a diameter that is equal to or less than a diameter of the distal end of the drainage tubing. Each aperture may be ovular or elongate in shape. The apertures may have a randomized or ordered arrangement around a circumference of the bell cap.

In another embodiment, the current invention is a percutaneous endoscopic gastrostomy tube apparatus for gastric sumping, comprising any one or more of the foregoing characteristics and features, individually or in combination.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1A:
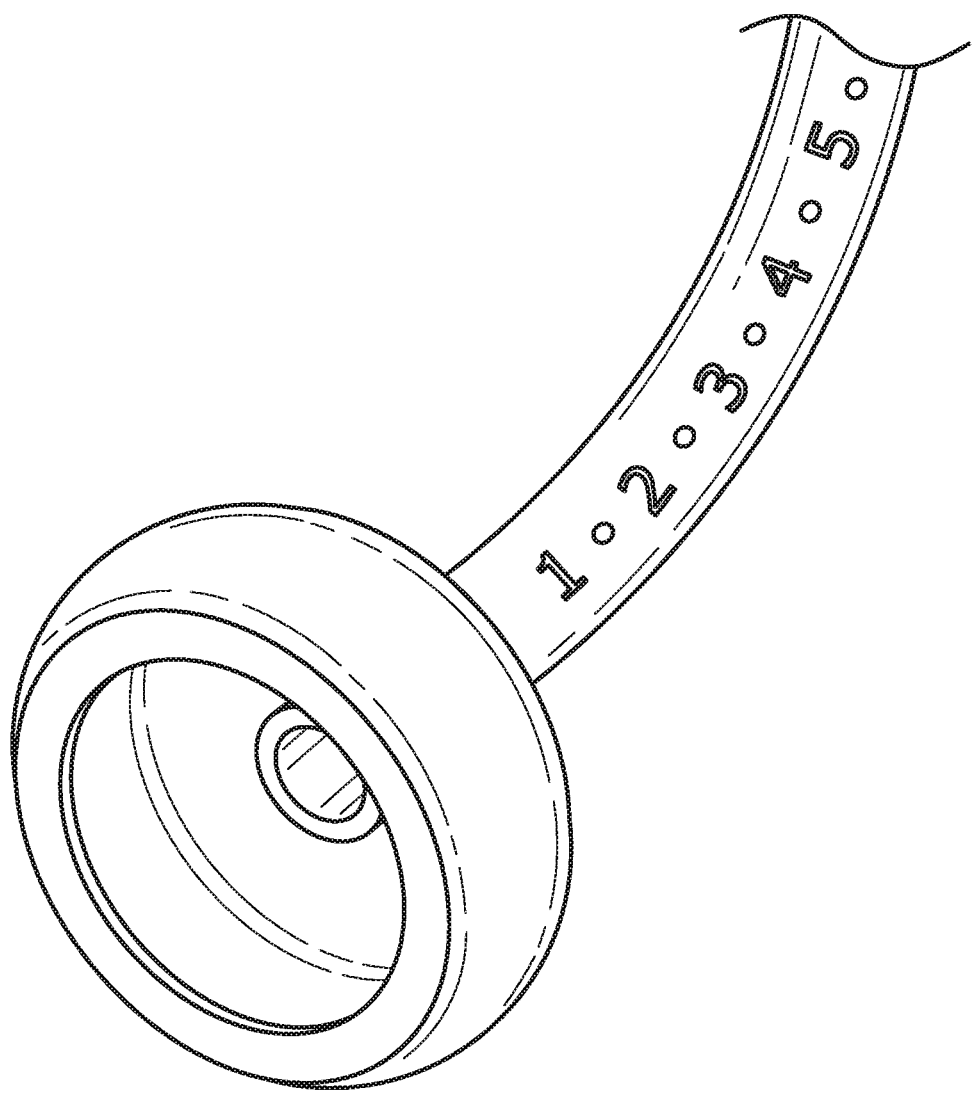
FIG. 1A depicts a conventional PEG tube.
Figure 1B:
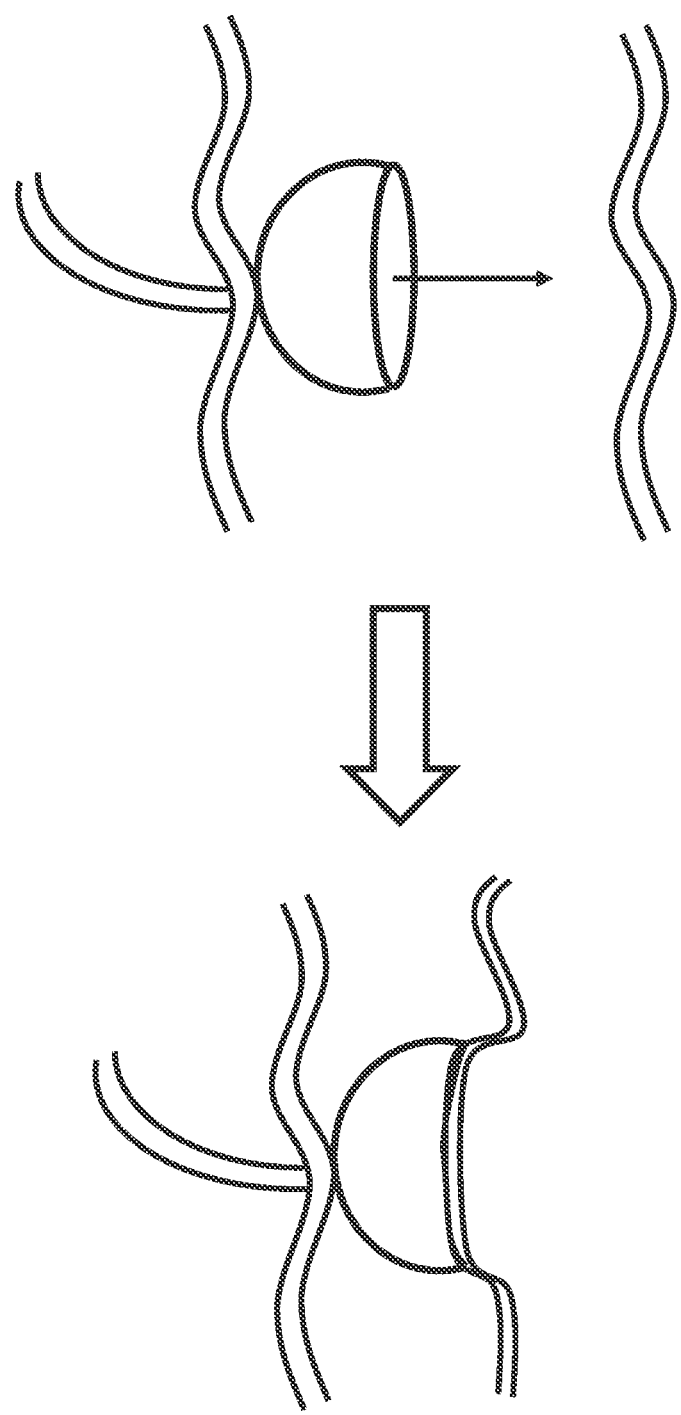
FIG. 1B depicts a conventional PEG tube contacting or suctioning the opposite abdominal wall, thus hindering further drainage from the stomach lumen.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

In certain embodiments, the current invention is a vented percutaneous endoscopic gastrostomy (PEG) tube and/or a method of performing percutaneous endoscopic gastronomy, substantially as discussed herein.

More particularly, the PEG tube includes an elongate, hollow drainage tubing having a proximal end and a distal end, where the term "proximal" refers to a position closer to the user or physician and "distal" refers to a position closer to the patient or subject in which the PEG tube is inserted. The tubing extends through the patient or subject's body with the distal end positioned in a region of interest (e.g., stomach lumen) within the patient or subject. A bell cap is coupled to the distal end of the drainage tubing, where the interior of the bell cap and the interior of the tubing are in open communication with each other. The bell cap includes a structural means or mechanism for ventilation that is positioned through and/or along a surface of the bell cap, such that the interior of the bell cap is in open communication with the external environment or gastric environment through the means of ventilation.

The bell cap can have a distal end that is open to the gastric (or visceral) environment. In this case, the means of ventilation may be a plurality of apertures disposed along the circumference of the body or distal end of the bell cap, such that the interior of the bell cap is in open communication with the external environment or gastric environment through the apertures. Each aperture may have a diameter that is equal to or slightly less than the diameter of the hollow drainage tubing. A slightly smaller diameter for each aperture would prevent debris from entering the interior of the bell cap and subsequently plugging or clogging the entrance to the drainage tubing.

Alternatively, the means of ventilation may be a plurality of notches or crenellations formed along an edge or lip of the distal end of the bell cap. Each notch or crenellation may have a width and/or length that is equal to or slightly less than the diameter of the hollow drainage tubing. A slightly smaller width and/or length for each notch or crenellation would prevent debris from entering the interior of the bell cap and subsequently plugging or clogging the entrance to the drainage tubing.

Alternatively, the means of ventilation may be a hemispherical arch attached to the bell cap at two (2) distinct points and extending distally to a distal apex positioned a spaced distance away from and distal to the distal edge of the bell cap. The two (2) distinct points of connection between the arch and bell cap can be positioned in diametric opposition to one another on the bell cap. There may also be a second hemispherical arch attached at another two (2) distinct points of the bell cap at a spaced distance away from and distal to the distal edge of the bell cap. These two (2) distinct points of connection can also be positioned in diametric opposition to one another on the bell cap. In this case, the hemispherical arches can intersect with each other at their distal apexes to form a ninety (90) degree angle between each other. They can intersect such that their distal apexes are the same distance away from and distal to the distal end of the bell cap. In other words, they would share a distal apex, as the apexes would be co-planar with each other. Alternatively, the hemispherical arches can cross each other such that they do not share a common distal apex; rather, one arch has a slightly longer length than the other and has a further distal apex than the other. In this case, they do not necessarily "intersect" each other at all but would be positioned on top of each other to cross each other (i.e., the distal apexes are not co-planar).

Alternatively, the bell cap can have a distal end that is closed to the external environment or gastric environment. In this case, the means of ventilation may be an array of apertures formed through and along the surface of the body and/or closed distal end of the bell cap. Each aperture may have a diameter that is equal to or slightly less than the diameter of the hollow drainage tubing. A slightly smaller diameter for each aperture would prevent debris from entering the interior of the bell cap and subsequently plugging or clogging the entrance to the drainage tubing.

Alternatively, each aperture in the closed bell cap can be ovular or elongate in shape.

Optionally, the hollow drainage tubing may be multichanneled, or in other words include a plurality of channels extending through the length of the drainage tubing. These channels would terminate in a single tapered cone at the tube end to be passed percutaneously. Once passed through the skin this cone would be transected, and a multi-port adapter would be attached to the extraluminal end of the tube.

EXAMPLES

The current invention is an improved PEG tube that allows continuous suctioning/sumping without occlusion of the tube by the gastric wall. The PEG tube minimizes, or completely eliminates, the need for a user thereof to frequently flush the tube, thus also curtailing intermittent suctioning and allowing for longer periods of uninterrupted drainage. Furthermore, the PEG tubes of the current invention reduce clogging of the tube by larger gastric matter that is intended to be suctioned out of the patient or subject. This benefit reduces the time burden on nursing by reducing the need for manual examination and clearing of the tube. Even with the improvements of the PEG tubs of the current invention, the tube still permits standard endoscopic placement and feeding/medication administration by the nurse or physician.

In certain embodiments, the current invention has a form similar to the classic mushroom cap "bell" of a conventional PEG tube but includes several structural and functional modifications and improvements for improved sumping and gastric suctioning, while minimizing the time and frequency of flushing out the PEG tube.

Figure 2A:
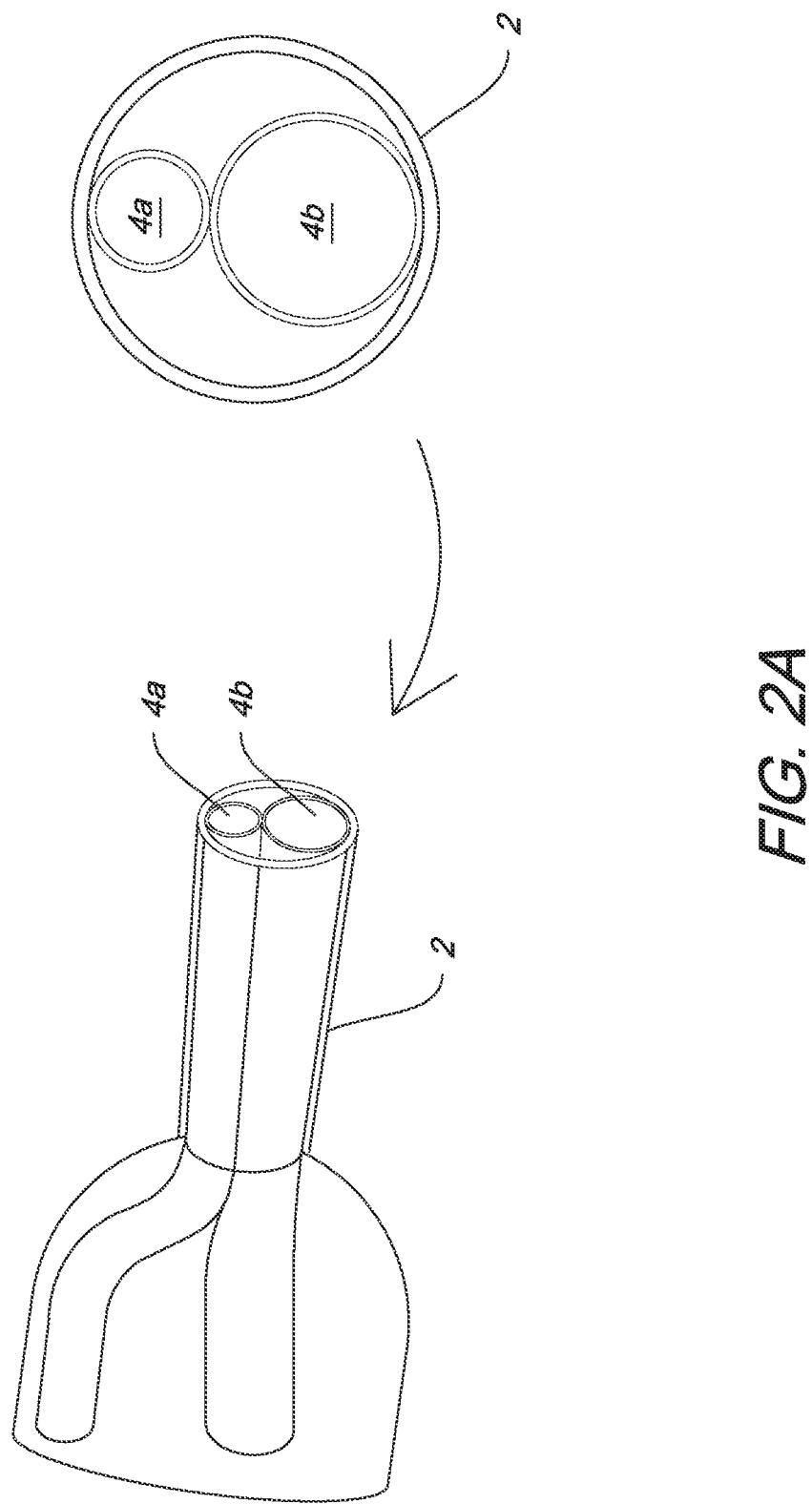
FIG. 2A depicts an optional multichannel component of the current invention.
Figure 2B:
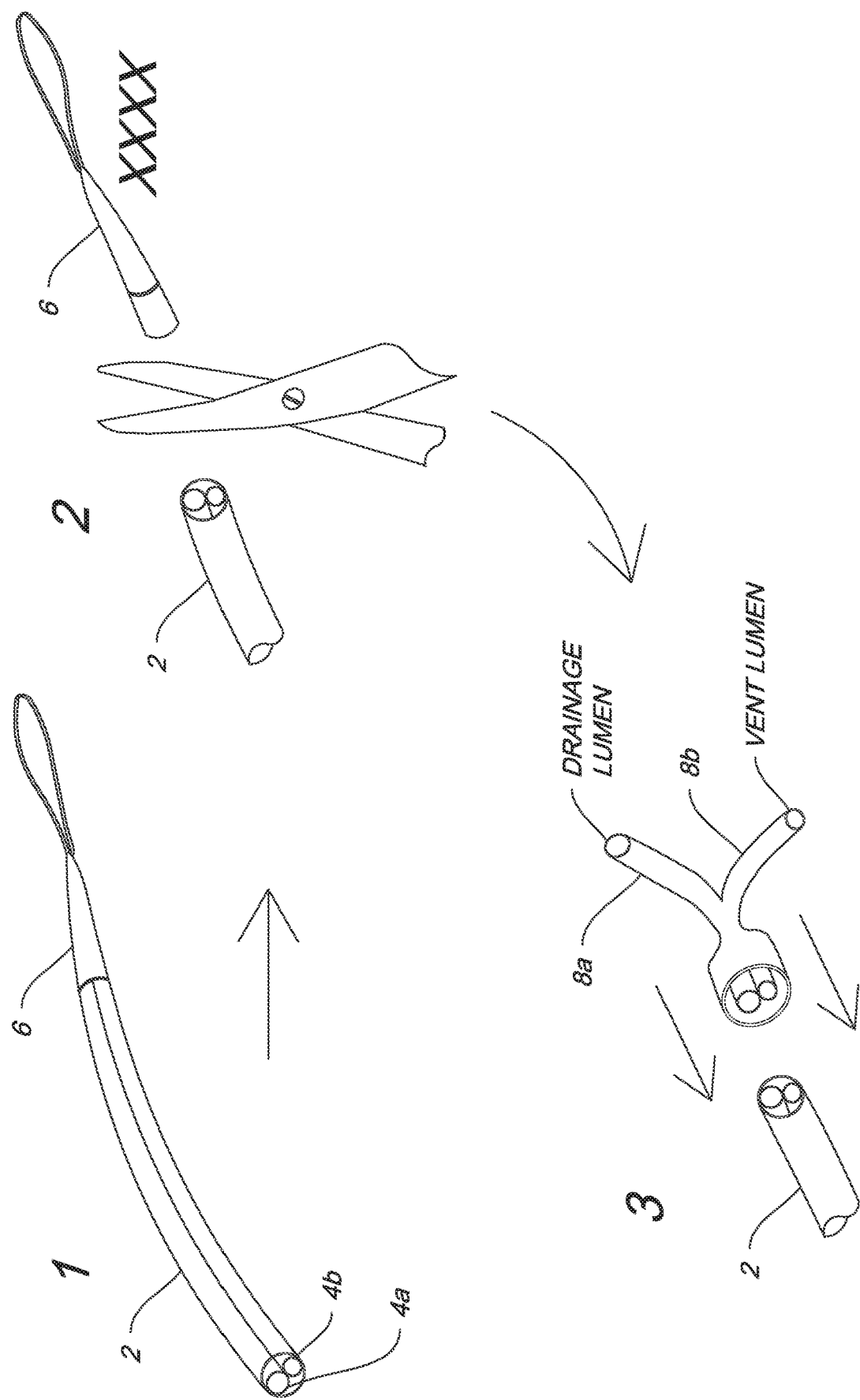
FIG. 2B depicts a mechanism and use of the optional multichannel component of the current invention.

As depicted in FIGS. 2A and 2B, hollow drainage tubing 2 can optionally be multichanneled (e.g., drainage channel 4a and ventricular channel 4b extending through the length of drainage tubing 2), with each channel 4a, 4b having the same or different diameters. Channels 4a, 4b may terminate in tapered cone 6 at the end of drainage tubing 2, to be passed percutaneously.

Drainage channel 4a is associated with the drainage lumen, and ventricular channel 4b is associated with the ventricular lumen. Once cone 6 is passed through the skin, cone 6 can be transected, and a multi-port adapter (formed of ports 8a, 8b) would be coupled to the extraluminal end of drainage tubing 2. Each lumen would respectively lead to one of ports 8a, 8b that split off drainage tubing 2, as seen in FIG. 2B. A multichannel PEG tube, such as this, performs similar to a nanogastric tube.

Figure 3A:
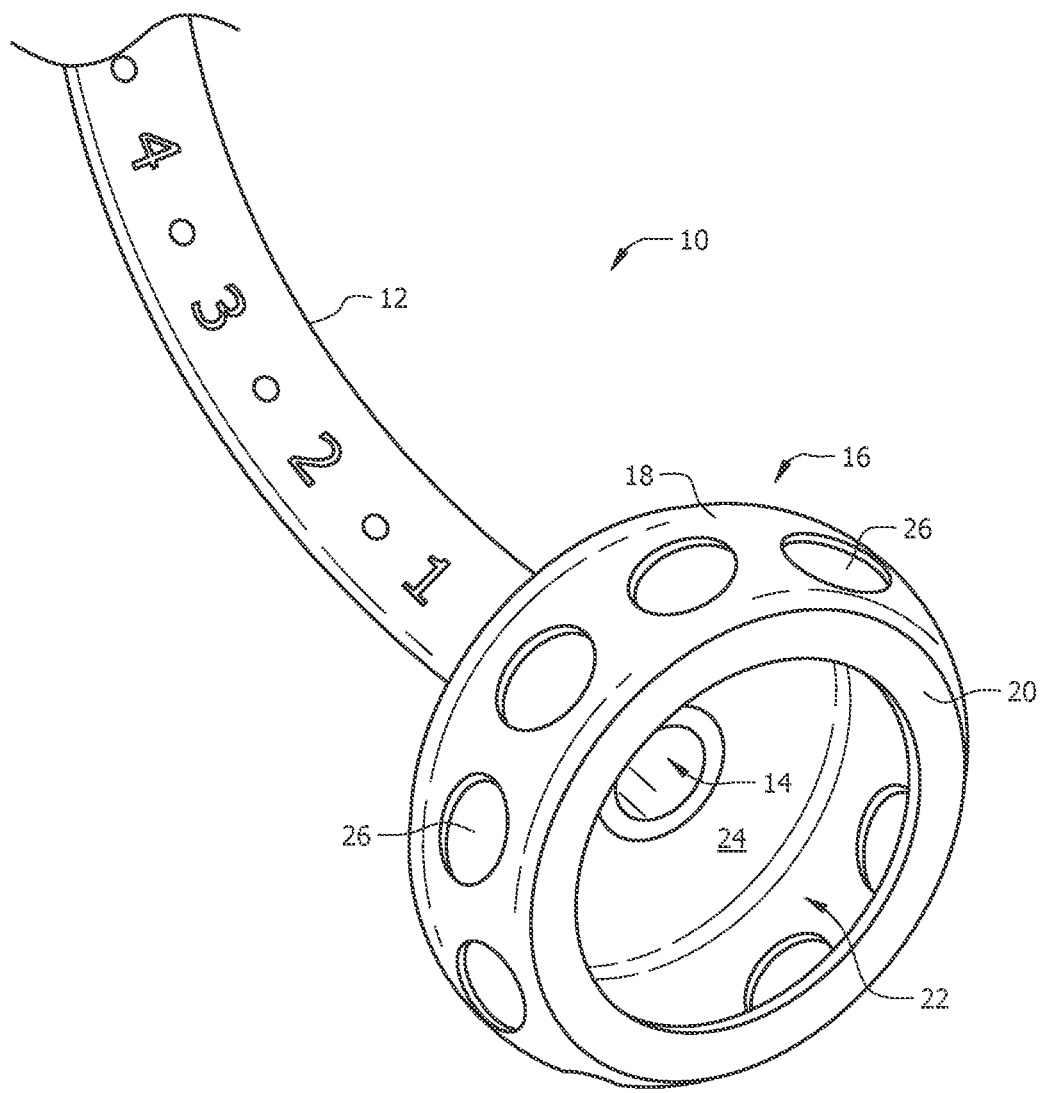
FIG. 3A depicts an embodiment of the current invention with apertures disposed around the hemispherical bell cap.
Figure 3B:
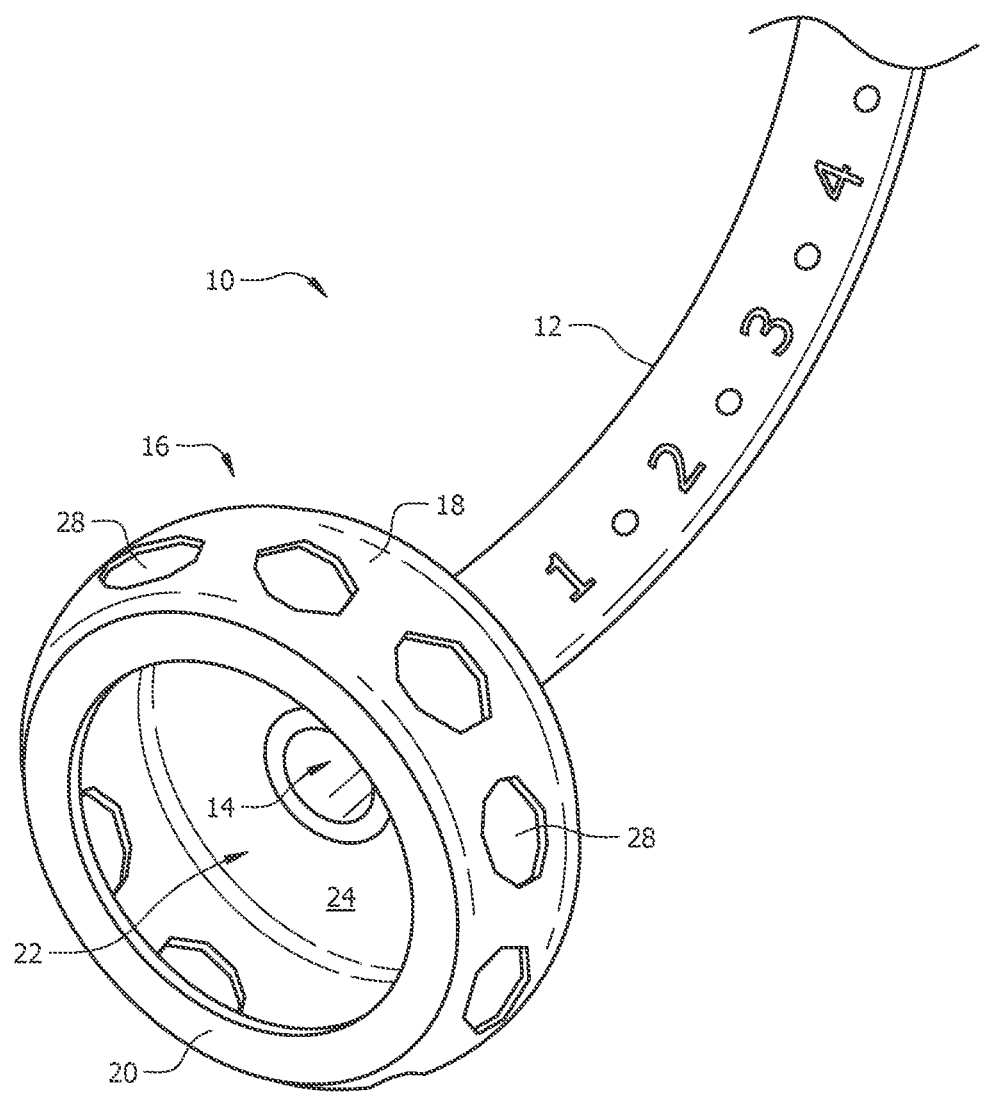
FIG. 3B depicts an alternate embodiment of the current invention, similar to that seen in FIG. 3A but with differently-shaped apertures.

Example 1 (FIGS. 3A-3B)

In an embodiment, the current invention is a PEG tube apparatus, generally denoted by the reference numeral 10, including elongate, hollow drainage tubing 12 and a bell cap, generally denoted by the reference numeral 16, in the form of a vented hemisphere. Hollow drainage tubing 12 has a proximal end closest to the nurse, physician or other user, and a distal end positioned within the stomach cavity/lumen of the patient or subject. Drainage tubing 12 includes distal tubing opening 14 that terminates in vented hemispherical bell cap 14.

Bell cap 16 includes body 18 and distal edge 20 formed around distal cap opening 22, which collectively form the boundaries of its hollow interior 24. Bell cap 16 is shaped as an inverted mushroom cap or is otherwise cylindrically shaped with its body 18 lined with a plurality of apertures 26, 28 formed radially around the entire circumference of body 18 of bell cap 14. Bell cap 16 has a proximal end connected to and in open communication with distal tubing opening 14 of hollow drainage tubing 12. Bell cap 16 further includes a distal end that is open to the external/gastric environment. Thus, the external/gastric environment is in open communication with hollow interior 24 of bell cap 16 through distal cap opening 22 and through apertures 26, 28 disposed around body 18 of bell cap 16.

Apertures 26, 28 disposed radially around the entire circumference of body 18 of bell cap 16 can have any shape (see circular shape in FIG. 3A and alternate/hexagonal shape in FIG. 3B) or size suitable for the function of PEG tube apparatus 10 or as desired by the user. Typically, though, each aperture 26, 28 may have a diameter that is about the same as or slightly smaller than the diameter of distal tubing opening 14 of hollow drainage tubing 12. This is done so that any particulates/matter that are suctioned through apertures 26, 28 into hollow interior 24 of bell cap 16 and subsequently into hollow drainage tubing 12 through distal opening 14 cannot be so large that they can block or clog drainage tubing 12, while still also maximizing the amount of particulates/matter that can be suctioned through bell cap 16 and drainage tubing 12 if distal cap opening 22 of bell cap 16 happens to be vacuum suctioned or sealed against an abdominal wall.

Figure 4:
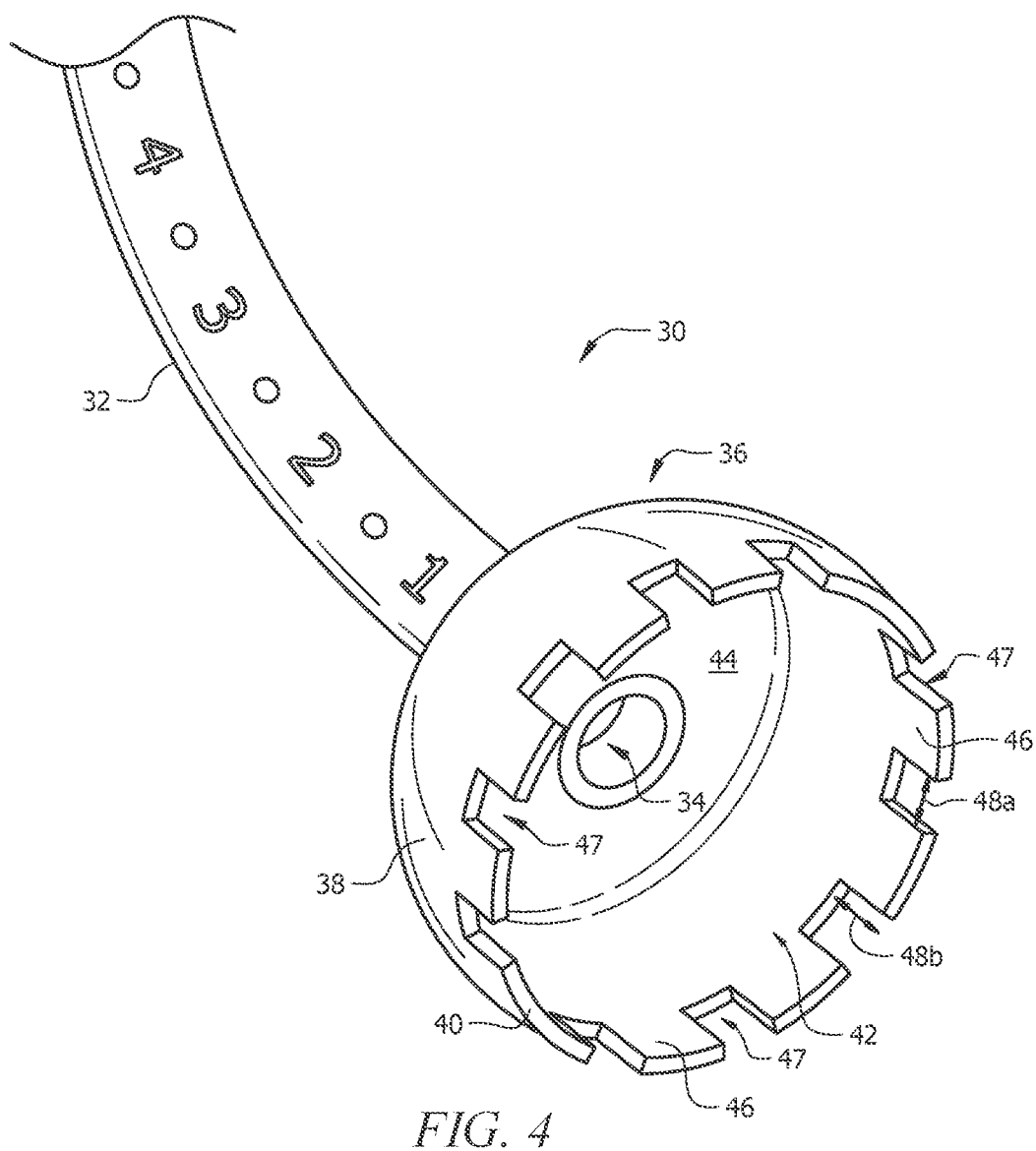
FIG. 4 depicts an embodiment of the current invention with crenellations disposed around the distal edge of the bell cap.

Example 2 (FIG. 4)

In an embodiment, the current invention is a PEG tube apparatus, generally denoted by the reference numeral 30, including elongate, hollow drainage tubing 32 and a bell cap, generally denoted by the reference numeral 36, in the form of a vented hemisphere. Hollow drainage tubing 32 has a proximal end closest to the nurse, physician or other user, and a distal end positioned within the stomach cavity/lumen of the patient or subject. Drainage tubing 32 includes distal tubing opening 34 that terminates in vented hemispherical bell cap 34.

Bell cap 36 includes body 38 and distal edge 40 formed around distal cap opening 42, which collectively form the boundaries of its hollow interior 44. Bell cap 36 is shaped as an inverted mushroom cap or is otherwise cylindrically shaped with its distal edge 40 lined with a plurality of crenellations or notches 46 formed radially around the entire circumference of the cap with corresponding grooves 47 formed between crenellations 46. Bell cap 36 has a proximal end connected to and in open communication with distal tubing opening 34 of hollow drainage tubing 32. Bell cap 36 further includes a distal end that is open to the external/gastric environment. Thus, the external/gastric environment is in open communication with hollow interior 44 of bell cap 36 through distal cap opening 42 and through grooves 47 disposed around distal edge 40 of bell cap 36.

Crenellations 46 disposed radially around the entire circumference of distal edge 40 of bell cap 36 can have any size suitable for the function of the PEG tube or as desired by the user. Typically, though, each groove 47 can have width 48a and/or length 48b that is about the same as or smaller than the diameter of hollow drainage tube 32 and distal opening 34 thereof. This is done so that any particulates/matter that are suctioned through grooves 47 into hollow interior 44 of bell cap 36 and subsequently into hollow drainage tubing 32 through distal opening 34 cannot be so large that they can block or clog drainage tubing 32, while still also maximizing the amount of particulates/matter that can be suctioned through bell cap 36 and drainage tubing 32 if distal cap opening 42 of bell cap 36 happens to be vacuum suctioned or sealed against an abdominal wall.

Figure 5A:
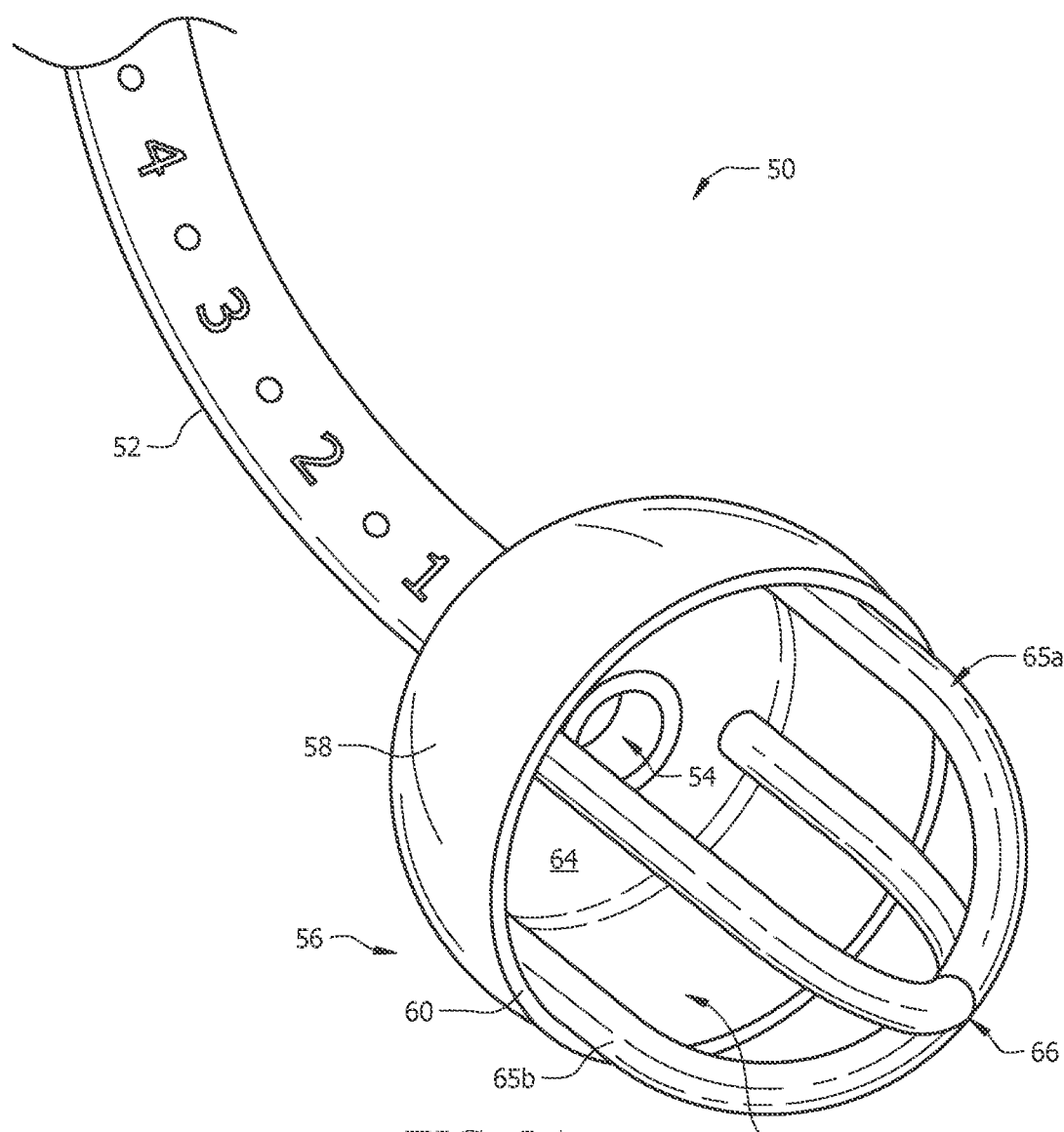
FIG. 5A depicts an embodiment of the current invention with hemispherical arches disposed on the bell cap.
Figure 5B:
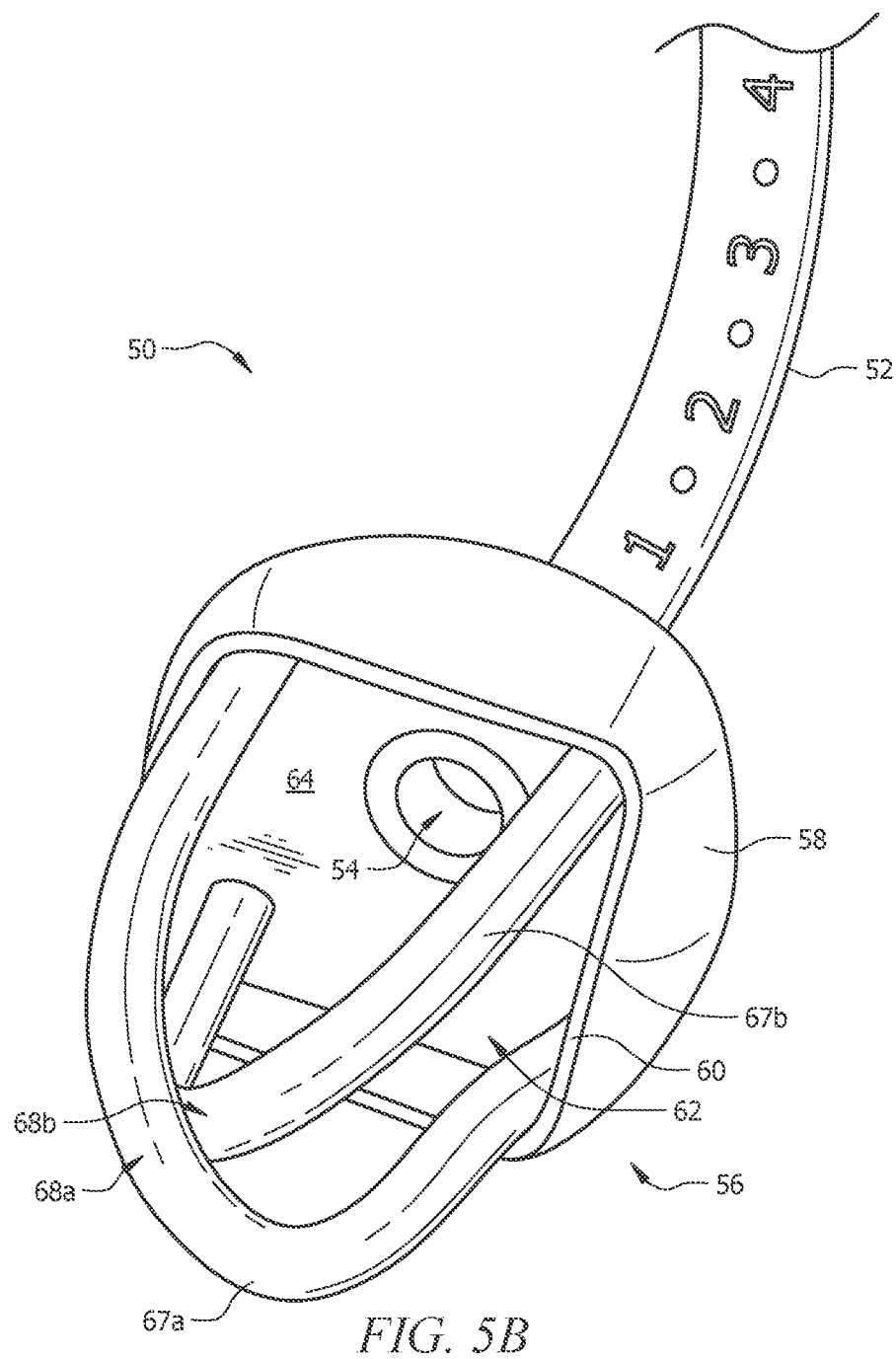
FIG. 5B depicts an alternate embodiment of the current invention, similar to that seen in FIG. 5A but with different apexes of the hemispherical arches.

Example 3 (FIGS. 5A-5B)

In an embodiment, the current invention is a PEG tube apparatus, generally denoted by the reference numeral 50, including elongate, hollow drainage tubing 52 and a bell cap, generally denoted by the reference numeral 56, in the form of a vented hemisphere or pseudo-sphere. Hollow drainage tubing 52 has a proximal end closest to the nurse, physician or other user, and a distal end positioned within the stomach cavity of the patient or subject. Drainage tubing 52 includes distal tubing opening 54 that terminates in vented hemispherical or pseudo-spherical bell cap 56.

Bell cap 56 includes body 58 and distal edge 60 formed around distal cap opening 62, which collectively form the boundaries of its hollow interior 64. Bell cap 56 is shaped as an inverted mushroom cap or is otherwise cylindrically shaped with one or more hemispherical arches 65a-65b (FIG. 5A), 67a-67b (FIG. 5B) attached to its distal edge 60. Bell cap 56 has a proximal end connected to and in open communication with distal tubing opening 54 of hollow drainage tubing 52. Bell cap 56 further includes a distal end that is open to the external/gastric environment. Thus, the external/gastric environment is in open communication with hollow interior 64 of bell cap 56 through distal cap opening 62 and through the space between hemispherical arches 65a-65b, 67a-67b.

First hemispherical arch 65a, 67a has a first end and a second end. The first end of hemispherical arch 65a, 67a is attached to a first side of bell cap 56 (e.g., at distal edge 60 of bell cap 56, at the proximal end of bell cap 56, along the exterior or interior surface of body 58 of bell cap 56, etc.). Hemispherical arch 65a, 67a follows a path of travel, extending distally from the first side of bell cap 56 until it reaches distal apex 66, 68a, (see FIG. 5A for apex 66 and FIG. 5B for apex 68a). Hemispherical arch 65a, 67a continues to follow its path of travel, extending proximally from its distal apex 66, 68a until it reaches a second side of the bell cap. As seen in FIGS. 5A-5B, the first and second sides of bell cap 56 typically are in diametric opposition to one another, or in other words are separated from one another by a distance equaling the diameter of the distal end of bell cap 56 if bell cap 56 has a circular distal end (see FIG. 5A). Alternatively, if bell cap 56 has another shape (e.g., rectangular, square, etc.), the arches extend from one side to an opposite side of the bell cap (see FIG. 5B).

In certain embodiments, second hemispherical arch 65b, 67b is connected to two (2) sides of bell cap 56 as well and extends distally from bell cap 56, similar to the connection and disposition of first hemispherical arch 65a, 67a. In this case, the arches can intersect with one another at any angle desired.

In an embodiment, however, first and second hemispherical arches 65a-65b, 67a-67b would intersect at approximately a ninety (90) degree angle, such that the paths of travel of arches 65a-65b, 67a-67b have planes that are perpendicular to each other. Arches 65a-65b can completely intersect, as in FIG. 5A where arches 65a-65b share common apex 66. Alternatively, arches 67a-67b can tangentially intersect, as in FIG. 5B, where first arch 67a includes distal apex 68a that is further distally positioned than second arch 67b, which includes distal apex 68b that is further proximally positioned than that of first arch 67a. Thus, first arch 67a also has a steeper pitch than second arch 67b.

Arches 65a-65b, 67a-67b are positioned along the distal end of bell cap 56 and form open spaces therebetween that are open distally to the external/gastric environment. Thus, the external/gastric environment is in open communication with hollow interior 64 of bell cap 56 through the space formed between arches 65a-65b, 67a-67b and the space between arches 65a-65b, 67a-67b and the distal end of bell cap 56.

The length of arches 65a-65b, 67a-67b and the space therebetween and between arches 65a-65b, 67a-67b and the distal end of bell cap 56 can have any size suitable for the function of PEG tube 50 or as desired by the user. Arches 65a-65b, 67a-67b, which can be circular or rounded in certain embodiments, help prevent distal edge 60 of bell cap 56 from vacuum suctioning or sealing against an abdominal wall, thus allowing continuous suctioning of the particulates/matter desired.

Figure 6A:
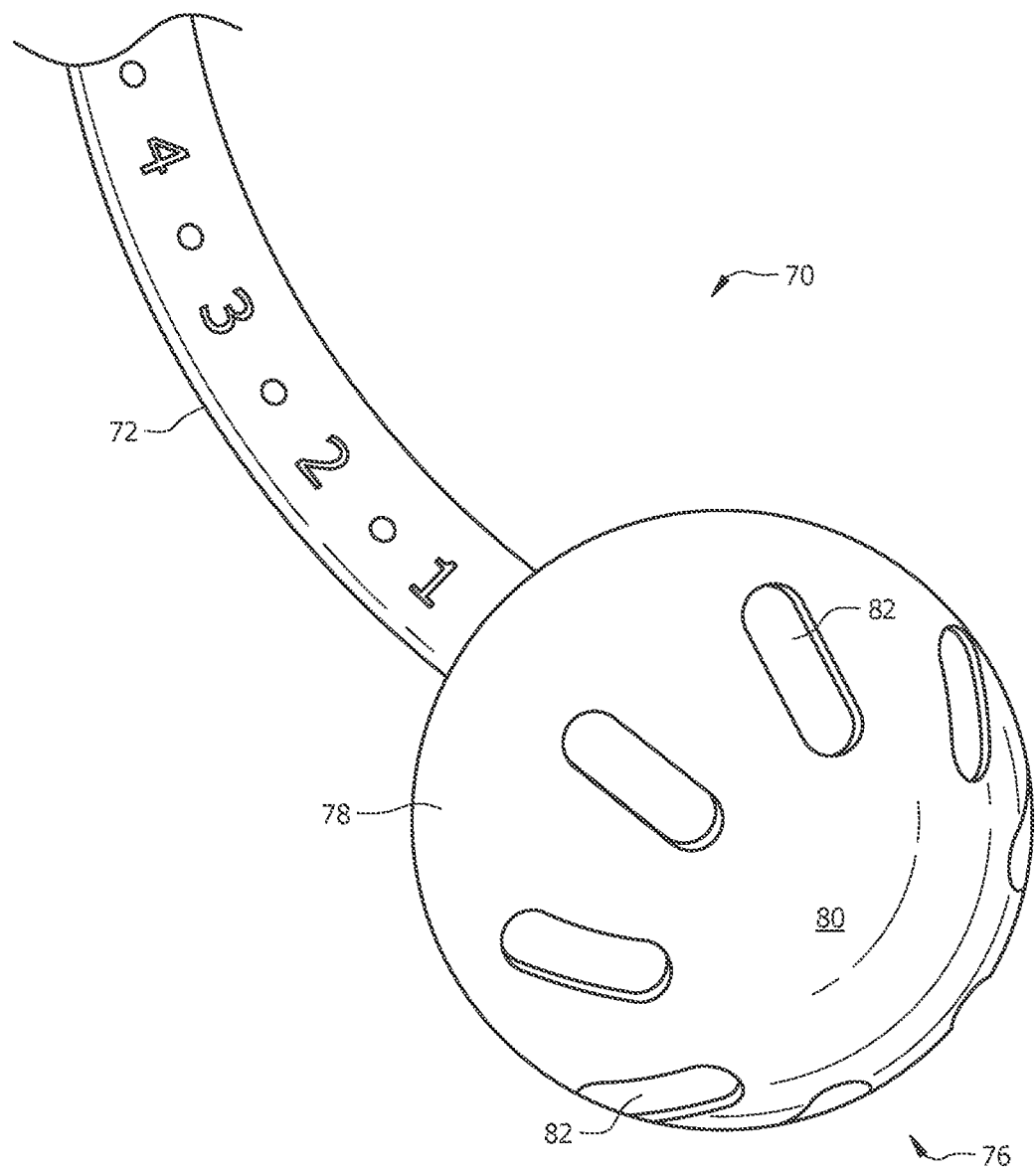
FIG. 6A depicts an embodiment of the current invention with apertures disposed around the spherical bell cap.
Figure 6B:
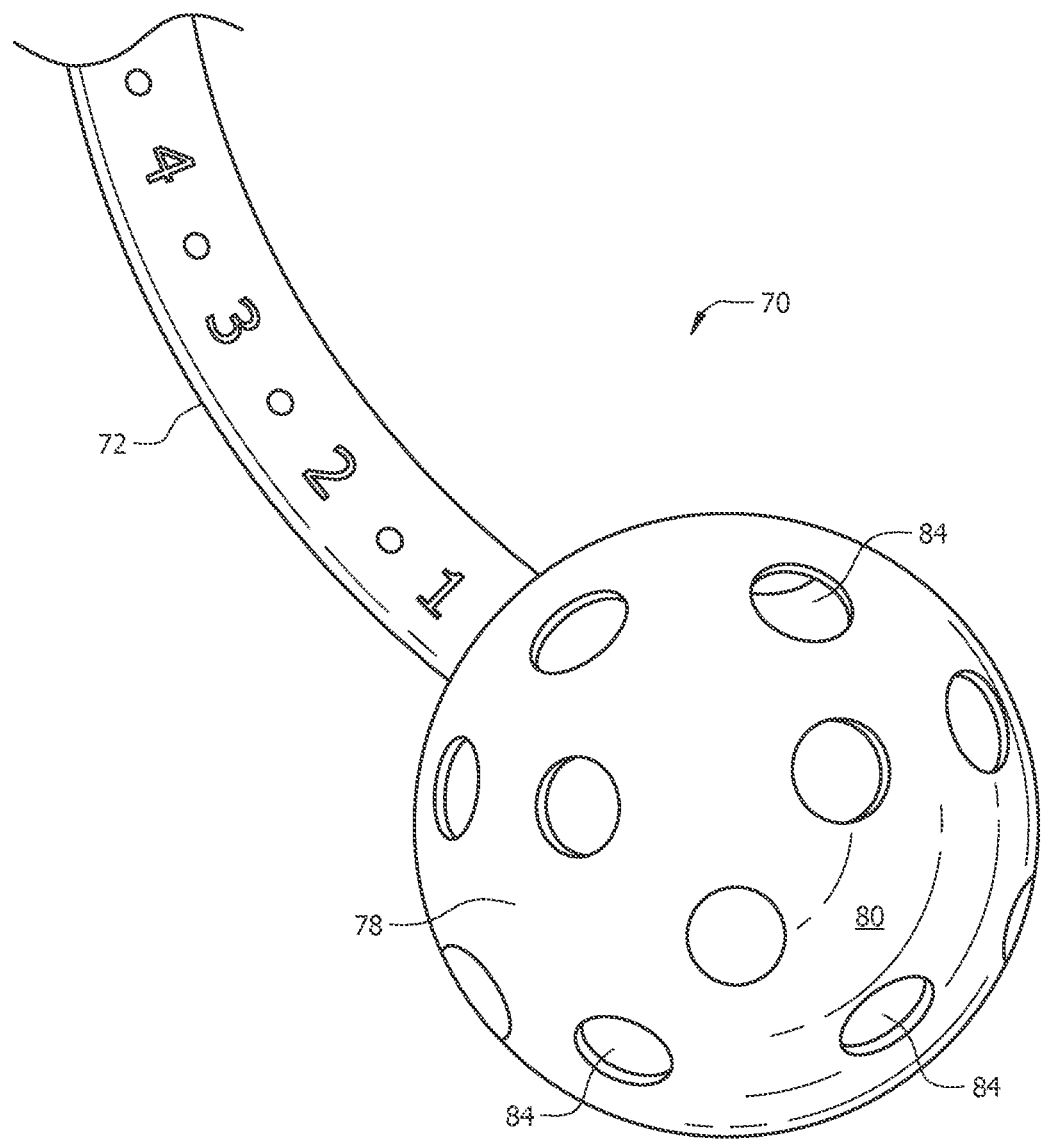
FIG. 6B depicts an alternate embodiment of the current invention, similar to that seen in FIG. 6A but with a randomized arrangement of the apertures.

Example 4 (FIGS. 6A-6B)

In an embodiment, the current invention is a PEG tube apparatus, generally denoted by the reference numeral 70, including elongate, hollow drainage tubing 72 and a bell cap, generally denoted by the reference numeral 76, in the form of a vented sphere. Hollow drainage tubing 72 has a proximal end closest to the nurse, physician or other user, and a distal end positioned within the stomach cavity of the patient or subject. Drainage tubing 72 includes a distal tubing opening (not shown in these figures but shown in previous figures) that terminates in the vented spherical bell cap.

Bell cap 76 includes body 78 and closed distal edge 80, which collectively form the boundaries of its hollow interior (not shown in these figures but shown in previous figures). Bell cap 76 is spherically- or otherwise cylindrically-shaped with a plurality of apertures 82, 84 formed within body 78 of bell cap 76. Bell cap 76 has a proximal end connected to and in open communication with the distal tubing opening of hollow drainage tubing 72. Bell cap 76 further includes distal edge 80 that is closed to the external/gastric environment. Apertures 82, 84 are formed generally along the distal end of bell cap 76 and along the sides of body 78 of bell cap 76 between the distal and proximal ends of bell cap 76. Apertures 82, 84 open outwardly to the external/gastric environment. Thus, the external/gastric environment is in open communication with the hollow interior of bell cap 76 through apertures 82, 84 disposed around body 78 of bell cap 76.

Apertures 82, 84 disposed around the surface or body 78 of bell cap 76 can have any size suitable for the function of the PEG tube or as desired by the user. In an embodiment, though, each aperture 82, 84 has a diameter or width that is about the same as or slightly smaller than the diameter of hollow drainage tube 72. This is done so that any particulates/matter that are suctioned through apertures 82, 84 into hollow drainage tubing 72 cannot be so large that they can block or clog drainage tubing 72, while still also maximizing the amount of particulates/matter that can be suctioned through bell cap 76 and drainage tubing 72 if certain apertures 82, 84 in bell cap 76 are vacuum suctioned or sealed against an abdominal wall.

Optionally, each aperture 82, 84 can be circular (see FIG. 6A) or elongate/ovular (see FIG. 6B). Further, each aperture 82, 84 can be randomized (see FIG. 6A) or ordered/aligned (see FIG. 6B).

Glossary of Claim Terms

Bell cap: This term is used herein to refer to the distal component or head of a PEG tube, through which matter or particulates from an anatomical region of interest are suctioned or sumped. It is contemplated herein that the bell cap can have any shape or form. Typically, the width or diameter of the bell cap is larger than the diameter of the proximally-positioned elongate, hollow drainage tubing attached thereto.

Closed to the external environment: This term is used herein to refer to a distal end of a bell cap having an edge that is closed or sealed, such as the side of a sphere.

Distal apex: This term is used herein to refer to the point of a hemispherical arch that is furthest away from a user (e.g., nurse, physician, etc.) of the PEG tube.

Distal: This term is used herein to refer to a relative position further from a nurse, physician, user, or other individual installing the PEG tube into a patient or subject Distinct points: This term is used herein to refer to different connection points on or along a bell cap of a PEG tube according to certain embodiments of the current invention.

External environment: This term is used herein to refer to the surroundings (e.g., gastric environment) of a PEG tube when inserted into a region of interest of a patient or subject.

Less: This term is used herein to refer to a size of an aperture that optimizes the balance between not clogging the drainage tube with excessively large particulates or matter, while still permitting larger size particulates or matter to be removed from the region of interest of the patient or subject.

Means of ventilating: This term is used herein to refer to a structural mechanism that provides additional points of communication between the interior of the bell cap and the external/gastric environment. Examples include, but are not limited to, apertures or slits in the bell cap, notches or crenellations along the distal edge of the bell cap, among other suitable structures that provide open communication between the bell cap interior and external/gastric environment.

Open communication: This term is used herein to refer to a relationship between two (2) structural components of a system, where a fluid would be able to freely travel from the interior of one component to the interior of the other component.

Open to the external environment: This term is used herein to refer to a distal end of a bell cap having an edge that is free, such as the wider portion of a hemisphere.

Ordered arrangement: This term is used herein to refer to the positioning of apertures having a clear pattern around a bell cap.

Proximal: This term is used herein to refer to a relative position closer to a nurse, physician, user, or other individual installing the PEG tube into a patient or subject.

Randomized arrangement: This term is used herein to refer to the positioning of apertures having no clear pattern around a bell cap.

Region of interest: This term is used herein to refer to an anatomical area within a patient or subject from which a user (e.g., physician, nurse, etc.) desires to remove particulates or matter or to which the user desires to place a feeding tube or administer medication. An example of a "region of interest" is a stomach lumen of the patient or subject.

Spaced distance: This term is used herein to refer to a predetermined length or distance between a lip on the distal end of a bell cap and the distal apex of a hemispherical arch attached thereto.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A percutaneous endoscopic gastrostomy tube, comprising:
    an elongate, hollow drainage tubing having a proximal end and a distal end, said hollow drainage tubing configured to extend through a body of a patient or subject with said distal end of said drainage tubing being positioned in a region of interest within said body of said patient or subject;
    a bell cap enclosing said distal end of said hollow drainage tubing, said bell cap having an outer surface establishing a substantially hollow interior that is in open communication with an interior of said hollow drainage tubing and a distal end that is open to an external environment, where in aid outer surface of said bell cap is a sphere when positioned in said region of interest within said body of said patient or subject; and
    a plurality of apertures disposed through the outer surface of the bell cap, wherein said plurality of apertures provides ventilation between said bell cap and said external environment.

2. A percutaneous endoscopic gastrostomy tube as in claim 1, wherein each aperture in said plurality of apertures has a diameter that is equal to or less than a diameter of said distal end of said drainage tubing.

3. A percutaneous endoscopic gastrostomy tube as in claim 1, wherein each aperture in said plurality of apertures has an opening that is smaller than an opening of said distal end of said drainage tubing.

4. A percutaneous endoscopic gastrostomy tube as in claim 1, wherein each aperture in said plurality of apertures is elongate in shape.

5. A percutaneous endoscopic gastrostomy tube as in claim 1, wherein each aperture in said plurality of apertures is located in a randomized arrangement about said outer surface of said bell cap.

6. A percutaneous endoscopic gastrostomy tube as in claim 1, wherein each aperture in said plurality of apertures is located in an ordered arrangement about said outer surface of said bell cap.

7. A percutaneous endoscopic gastrostomy tube, comprising:
    an elongate, hollow drainage tubing having a proximal end and a distal end, said hollow drainage tubing configured to extend through a body of a patient or subject with said distal end of said drainage tubing being positioned in a region of interest within said body of said patient or subject;
    a bell cap enclosing said distal end of said hollow drainage tubing, said bell cap having an outer surface establishing a substantially hollow interior that is in open communication with an interior of said hollow drainage tubing, wherein said outer surface of said bell cap is a sphere when positioned in said region of interest within said body of said patient or subject;
    a plurality of apertures disposed through the outer surface of the bell cap, wherein said plurality of apertures provides ventilation between said bell cap and an external environment; and
    each aperture in said plurality of apertures having an opening that is smaller than an opening of said distal end of said drainage tubing.

8. A percutaneous endoscopic gastrostomy tube as in claim 7, wherein each aperture in said plurality of apertures has a diameter that is less than a diameter of said distal end of said drainage tubing.

9. A percutaneous endoscopic gastrostomy tube as in claim 7, wherein each aperture in said plurality of apertures is elongate in shape.

10. A percutaneous endoscopic gastrostomy tube as in claim 7, wherein each aperture in said plurality of apertures is located in a randomized arrangement about said outer surface of said bell cap.

11. A percutaneous endoscopic gastrostomy tube as in claim 7, wherein each aperture in said plurality of apertures is located in an ordered arrangement about said outer surface of said bell cap.

* * * * *